United States Patent
Dyke et al.

(10) Patent No.: US 6,313,116 B1
(45) Date of Patent: Nov. 6, 2001

(54) BENZOTHIAZOLE COMPOUNDS AND THEIR THERAPEUTIC USE

(75) Inventors: Hazel Joan Dyke; Andrew Sharpe; Hannah Jayne Kendall; Richard John Davenport; Verity Margaret Sabin; George Martin Buckley; Marianna Dilani Richard; Alan Findlay Haughan, all of Cambridge (GB)

(73) Assignee: Darwin Discovery, Ltd. (GB)

( * ) Notice: Subject to any disclaimer, the term of this patent is extended or adjusted under 35 U.S.C. 154(b) by 0 days.

(21) Appl. No.: 09/780,911

(22) Filed: Feb. 9, 2001

(30) Foreign Application Priority Data

Feb. 11, 2000 (GB) .................................................. 0003254

(51) Int. Cl.[7] .................. A61K 31/428; A61K 31/5377; C07D 277/64; C07D 413/04

(52) U.S. Cl. ................................. 514/233.8; 514/254.02; 514/321; 514/367; 544/135; 544/368; 546/198; 548/178

(58) Field of Search ............................ 548/178; 546/198; 544/135, 368; 514/233.8, 254.02, 321, 367

(56) References Cited

FOREIGN PATENT DOCUMENTS 98-22460-A1 * 5/1998 (WO) .
99-24035-A1 * 5/1999 (WO) .

* cited by examiner

*Primary Examiner*—Laura L. Stockton
(74) *Attorney, Agent, or Firm*—Saliwanchik, Lloyd & Saliwanchik

(57) ABSTRACT

Compounds that are inhibitors of phosphodiesterase and have therapeutic utility, are of formula (i)

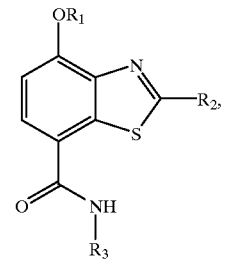

(i)

wherein $R_1$ is $C_{3-6}$ cycoalkyl, or $C_{1-3}$ alkyl optionally substituted with one or more fluorine atoms;

$R_2$ is $C_{1-6}$ alkyl, $C_{3-6}$ cycloalkyl, $CF_3$, $CH_2CF_3$, $C_2F_5$ or $NR_4R_5$;

$R_3$ is a pyrazole, imidazole or isoxazole group of partial formula (A), (B) or (C)

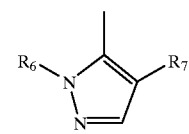

(A)

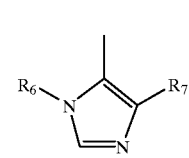

(B)

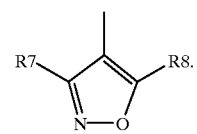

(C)

$NR_4R_5$ is a nitrogen-containing heterocyclic ring;

$R_6$ is $C_{1-3}$ alkyl; and $R_7$ and $R_8$, which are the same or different, are each H, $C_{1-3}$ alkyl, halogen, $CF_3$ or CN, provided that both are not H;

or a pharmaceutically-acceptable salt thereof

17 Claims, No Drawings

BENZOTHIAZOLE COMPOUNDS AND THEIR THERAPEUTIC USE

FIELD OF THE INVENTION

The present invention relates to novel heterocyclic compounds and to their formulation and use as pharmaceuticals.

BACKGROUND OF THE INVENTION

The modes of action of phosphodiesterases and also tumour necrosis factors (TNF), and the therapeutic utilities of inhibitors thereof, are described in WO-A-97/44036 and U.S. Pat. No. 5,804,588, the contents of which are incorporated herein by reference. WO-A-98/22460 and U.S. patent application Ser. No. 09/422,473, filed Nov. 17, 1997, disclose benzothiazoles that also have such activity.

SUMMARY OF THE INVENTION

This invention provides novel compounds having therapeutic utility, in particular for the treatment of disease states associated with proteins which mediate cellular activity, for example by inhibiting TNF and/or PDE IV. According to the invention, novel compounds are of formula (i):

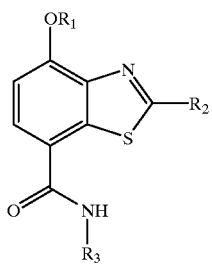

(i)

wherein $R_1$ is $C_{3-6}$ cycloalkyl, or $C_{1-3}$ alkyl optionally substituted with one or more fluorine atoms;

$R_2$ is $C_{1-6}$ alkyl, $C_{3-6}$ cycloalkyl, $CF_3$, $CH_2CF_3$, $C_2F_5$ or $NR_4R_5$;

$R_3$ is a pyrazole, imidazole or isoxazole group of partial formula (A), (B) or (C)

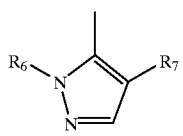

(A)

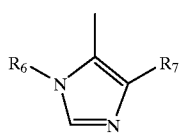

(B)

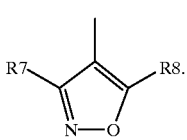

(C)

$NR_4R_5$ is a nitrogen-containing heterocyclic ring, such as morpholine, pyrrolidine, piperidine, N-methylpiperazine or azetidine;

$R_6$ is $C_{1-3}$ alkyl; and $R_7$ and $R_8$, which are the same or different, are each H, $C_{1-3}$ alkyl, halogen, $CF_3$ or CN, provided that both are not H;

or a pharmaceutically-acceptable salt thereof.

In summary, the compounds of the invention represent a selection within the scope of WO-A-98/22460. The novel compounds have superior potency.

This invention provides also a method for mediating or inhibiting the enzymatic activity or catalytic activity of PDE IV in a mammal in need thereof and for inhibiting the production of TNF in a mammal in need thereof, which comprises administering to said mammal an effective amount of a compound of Formula (i) or a pharmaceutically-acceptable salt thereof.

DESCRIPTION OF THE INVENTION

The term "$C_{1-6}$ alkyl" means a straight or branched chain alkyl moiety having one to six carbon atoms, including, for example, methyl, ethyl, propyl, isopropyl, n-butyl, isobutyl, sec-butyl, tert-butyl, pentyl, hexyl and the like. The term "$C_{1-3}$ alkyl" includes, for example, methyl, ethyl, propyl and isopropyl.

The term "$C_{3-6}$ cycloalkyl" includes, for example, cyclopropyl, cyclobutyl, cyclopropyl, cyclopentyl and cyclohexyl.

The term "halogen" includes, for example, fluorine, chlorine, bromine and iodine.

In one embodiment of the invention, $R_1$ is optionally F-substituted alkyl, and $R_2$ is alkyl, cycloalkyl, $CF_3$ or $NR_4R_5$. In a preferred group of compounds of formula (i), $R_1$ is $CH_3$ or $CHF_2$. In the same or another preferred group of compounds of formula (i), $R_2$ is $CF_3$, ethyl or cyclopropyl.

$R_3$, in compounds of the invention, may in particular be a pyrazole of partial formula (A) or an isoxazole of partial formula (C). When $R_3$ is a pyrazole moiety, $R_6$ is especially $CH_3$ and $R_7$ is particularly CN, $CH_3$ or $CF_3$. Where $R_3$ is an isoxazole moiety, $R_7$ is especially $CH_3$, $CF_3$ or CN, and $R_8$ is particularly $CH_3$, $CF_3$ or CN.

Particularly useful compounds of the invention are those of Examples 1 to 15, below. Especially useful compounds include:

4-methoxy-2-trifluoromethylbenzothiazole-7-carboxylic acid (4-cyano-2-methyl-2H-pyrazole-3-yl)amide and 2-cyclopropyl-4-methoxybenzothiazole-7-carboxylic acid (4-cyano-2-methyl-2H-pyrazole-3-yl)amide.

Certain of the compounds of formula (i) which contain a basic group form acid addition salts. Suitable acid addition salts include pharmaceutically-acceptable inorganic salts such as the sulphate, nitrate, phosphate, borate, hydrochloride and hydrobromide, and pharmaceutically-acceptable organic acid addition salts such as acetate, tartrate, maleate, citrate, succinate, benzoate, ascorbate, methanesulphate, 60-ketoglutarate, α-glycerophosphate and glucose-1-phosphate. The pharmaceutically-acceptable salts of the compounds of formula (i) are prepared using conventional procedures.

Compounds of the invention may be prepared by reaction of an appropriate carboxylic acid of formula (ii) with a suitable amine $R_3NH_2$ as described in WO-A-98/22460. Carboxylic acids of formula (ii) are prepared from a compound of formula (iii) using standard conditions known to those skilled in the art, either by formylation to provide an aldehyde of formula (iv) followed by an oxidation to provide an acid of formula (ii), or by bromination to provide bromide of formula (v) followed by carboxylation to provide an acid of formula (ii). Examples of these methods are described in WO-A-98/22460. Amines R₃NH₂ may be commercially available, previously described compounds, or are prepared using standard conditions known to those skilled in the art.

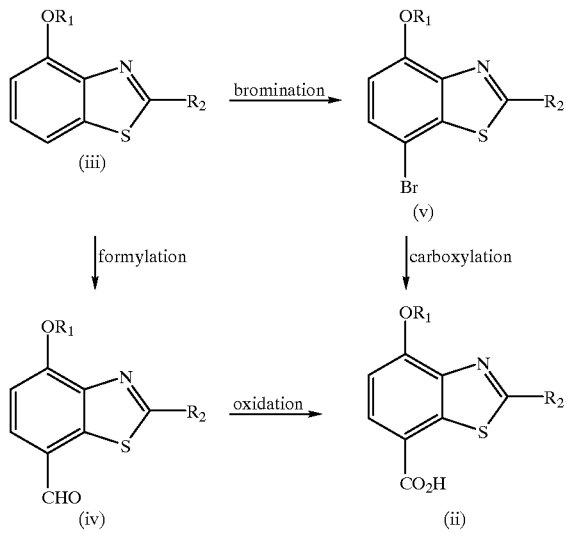

Compounds of formula (iii) or (v) may be prepared from amine (vi) in one of two general methods known to those skilled in the art. Compounds of formula (iii) in which R₂ represents alkyl, cycloalkyl or CF₃ may be prepared as follows. Amine (vi) may be subjected to ring-opening to provide amino-thnol (vii), which may be condensed with anappropiate carboxylic acid or triethylorthopropionate to provide compounds of formula (iii). Alternatively, compounds of formula (v) in which R₂ represents NR₄R₅ may be prepared from amine (vi) by diazotisation/bromination to give bromide (vii), followed by bromination to give dibromide (ix). Subsequent treatment with an appropriate nitrogen-containing aliphatic heterocycle, such as mobpholine, provides compounds of formula (v).

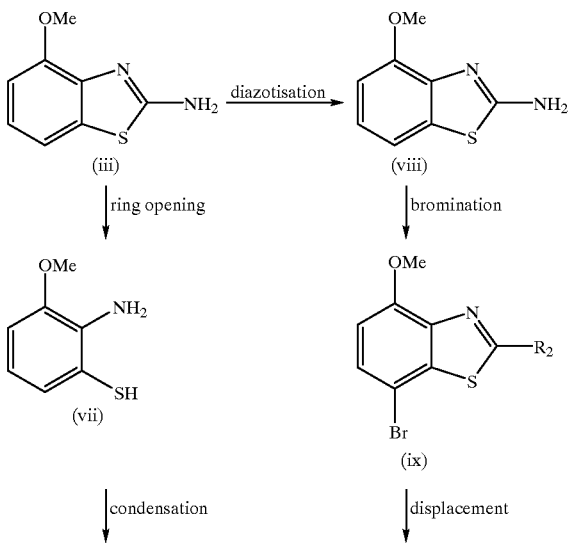

-continued

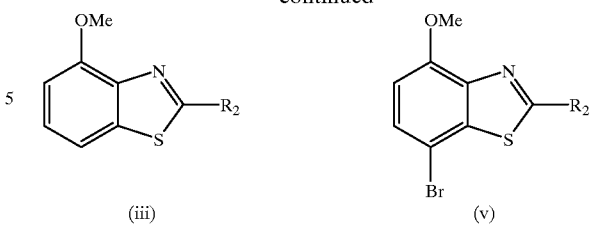

For example, benzthiazole (vi) can be ring-opened using any standard conditions known to those skilled in the art, for example by refluxing in sodium hydroxide solution. Treatment of the resulting compound with an appropriate carboxylic acid using any suitable conditions known to those skilled in the art provides a compound of formula (iii). Suitable conditions include the use of trimethylsilylpolyphosphate in 1,2-dichlorobenzene. To prepare a compound of formula (v), standard conditions are utilised. Thus diazotisation/bromination may be effected using any appropriate conditions, for example by using potassium bromide and sodium nitrite in sulphuric acid. Bromination may be achieved using, for example N-bromosuccinimde in acetonitrile. Displacement of the 2-bromo substituent may be carried out by treating dibromide (ix) with the appropriate cyclic amine. Elevated temperatures may favourably be employed for this reaction.

The invention includes the prevention and treatment of TNF-mediated disease or disease states, by which is meant any and all disease states in which TNF plays a role, either by production of TNF itself, or by TNF causing another cytokine to be released, such as but not limited to IL-1 or IL-6. A disease state in which IL-1, for instance, is a major component, and whose production or action is exacerbated or secreted in response to TNF, would therefore be considered a disease state mediated by TNF. As TNF-β (also known as lymphotoxin) has close structural homology with TNF-α (also known as cachectin), and since each induces similar biological responses and binds to the same cellular receptor, both TNF-α and TNF-β are inhibited by compounds of the present invention and thus are herein referred to collectively as "TNF" unless specifically delineated otherwise.

PDE IV inhibitors are useful in the treatment of a variety of allergic and inflammatory diseases, including: asthma, chronic bronchitis, atopic dermatitis, atopic eczema, urticaria, allergic rhinitis, allergic conjunctivitis, vernal conjunctivitis, inflammation of the eye, allergic responses in the eye, eosinophilic granuloma, psoriasis, Bechet's disease, erythematosis, anaphylactoid purpura nephritis, joint inflammation, arthritis, rheumatoid arthrtis and other arthritic conditions such as rheumatoid spondylitis and osteoarthritis, septic shock, ulcerative colitis, Crohn's disease, reperfusion injury of the myocardium and brain, chronic glomerulonephritis, endotoxic shock and adult respiratory distress syndrome. In addition, PDE IV inhibitors are useful in the treatment of diabetes insipidus and conditions associated with cerebral metabolic inhibition, such as cerebral senility, senile dementia (Alzheimer's disease), memory impairment associated with Parkinson's disease, depression and multi-infarct dementia. PDE IV inhibitors are also useful in conditions ameliorated by neuroprotectant activity, such as cardiac arrest, stroke and intermittent claudication. Additionally, PDE IV inhibitors could have utility as gastroprotectants. A special embodiment of the therapeutic methods of the present invention is the treatment of asthma.

The viruses contemplated for treatment herein are those that produce TNF as a result of infection, or those which are sensitive to inhibition, such as by decreased replication, directly or indirectly, by the TNF inhibitors of Formula (i). Such viruses include, but are not limited to HIV-1, HIV-2 and HIV-3, cytomegalovirus (CMV), influenza, adenovirus and the Herpes group of viruses, such as, but not limited to, Herpes zoster and Herpes simplex.

This invention more specifically relates to a method oftreating a mammal, afflicted with a human immunodeficiency virus (HIV), which comprises administering to such mammal an effective TNF inhibiting amount of a compound of Formula (i) or a pharmaceutically-acceptable salt thereof.

The compounds of this invention may be also be used in association with the veterinary treatment of animals, other than humans, in need of inhibition of TNF production. TNF mediated diseases for treatment, therapeutically or prophylactically, in animals include disease states such as those noted above, but in particular viral infections. Examples of such viruses include, but are not limited to feline immunodeficiency virus (FIV) or other retroviral infection such as equine infectious anaetmia virus, caprine arthritis virus, visna virus, maedi virus and other lentiviruses.

The compounds of this invention are also useful in treating parasite, yeast and fungal infections, where such yeast and fungi are sensitive to upregulation by TNF or will elicit TNF production in vivo. A preferred disease state for treatment is fungal meningitis.

The compounds of formula (i) are preferably in pharmaceutically-acceptable form. By pharmaceutically-acceptable form is meant, infer alia, a pharmaceutically-acceptable level of purity excluding normal pharmaceutical additives such as diluents and carriers, and including no material considered toxic at normal dosage levels. A pharmaceutically-acceptable level of purity will generally be at least 50% excluding normal pharmaceutical additives, preferably 75%, more preferably 90% and still more preferably 95%. When used herein the term "pharmaceutically-acceptable" encompasses materials suitable for both human and veterinary use.

A compound of formula (i) or where appropriate a pharmaceutically-acceptable salt thereof and/or a pharmaceutically-acceptable solvate thereof, may be administered per se or, preferably, as a pharmaceutical composition also comprising a pharmaceutically-acceptable carrier.

Accordingly, the present invention provides a pharmaceutical composition comprising a compound of formula (i) or where appropriate a pharmaceutically-acceptable salt thereof and/or a pharmaceutically-acceptable solvate thereof, and a pharmaceuticay-acceptable carrier.

The active compound may be formulated for administration by any suitable route, the preferred route depending upon the disorder for which treatment is required, and is preferably in unit dosage form or in a form that a human patient may administer to himself in a single dosage. Advantageously, the composition is suitable for oral, rectal, topical, parenteral administration or through the respiratory tract. Preparations may be designed to give slow release of the active ingredient.

The term parenteral as used herein includes subcutaneous injections, intravenous, intramuscular, intrasternal injection or infusion techniques. In addition to the treatment of warm-blooded animals such as mice, rats, horses, cattle, sheep, dogs, cats, etc, the compounds of the invention are effective in the treatment of humans.

The compositions of the invention may be in the form of tablets, capsules, sachets, vials, powders, granules, lozenges, suppositories, reconstitutable powders, or liquid preparations such as oral or sterile parenteral solutions or suspensions. Topical formulations are also envisaged where appropriate.

In order to obtain consistency of administration it is preferred that a composition of the invention is in the form of a unit dose. Unit dose presentation forms for oral administration may be tablets and capsules and may contain conventional excipients such as binding agents, for example syrup, acacia, gelatin, sorbitol, tragacanth, or polyvinylpyrrolidone; fillers for example microcrystalline cellulose, lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; orpharmaceutically-acceptable wetting agents such as sodium lauryl sulphate.

Solid oral compositions may be prepared by conventional methods of blending, filling, tabletting or the like. Repeated blending operations may be used to distribute the active agent throughout those compositions employing large quantities of fillers.

Such operations are of course conventional in the art. The tablets may be coated according to methods well known in normal pharmaceutical practice, in particular with an enteric coating.

Oral liquid preparations may be in the form of, for example, emulsions, syrups or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia, non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

Compositions may also suitably be presented for administration to the respiratory tract as a snuff or an aerosol or solution for a nebuliser, or as a microfine powder for insufflation, alone or in combination with an inert carrier such as lactose. In such a case the particles of active compound suitably have diameters of less than 50 $\mu$m, such as from 0.1, to 50 $\mu$m, preferably less than 10 $\mu$m, for example from 1 to 10 $\mu$m, 1 to 5 $\mu$m or from 2 to 5 $\mu$m. Where appropriate, small amounts of other anti-asthmatics and bronchodilators for example sympathomimetic amines such as isoprenaline, isoetharine, salbutamol, phenylephrine and ephedrine; corticosteroids such as prednisolone and adrenal stimulants such as ACTH may be included.

For parenteral administration, fluid unit dosage forms are prepared utilizing the compound and a sterile vehicle, and, depending on the concentration used, can be either suspended or dissolved in the vehicle. In preparing solutions, the compound can be dissolved in water for injection and filter-sterilised before filling into a suitable vial or ampoule and sealing.

Advantageously, adjuvants such as a local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10–60% by weight, of the active material, depending on the method of administration.

Compounds of formula (i), or if appropriate a pharmaceutically-acceptable salt thereof and/or a pharmaceutically-acceptable solvate thereof may also be administered as a topical formulation in combination with conventional topical excipients.

Topical formulations may be presented as, for instance, ointments, creams or lotions, impregnated dressings, gels, gel sticks, spray and aerosols, and may contain appropriate conventional additives such as preservatives, solvents to assist drug penetration and emollients in ointments and creams. The formulations may contain compatible conventional carriers, such as cream or ointment bases and ethanol or oleyl alcohol for lotions.

Suitable cream, lotion, gel, stick, ointment, spray or aerosol formulations that may be used for compounds of formula (i) or if appropriate a pharmaceutically-acceptable salt thereof, are conventional formulations well known in the art, for example, as described in standard text books such as Harry's Cosmeticology published by Leonard Hill Books, Remington's Pharmaceutical Sciences, and the British and US Pharmacopoeias.

Suitably, the compound of formula (i), or if appropriate a pharmaceutically-acceptable salt thereof, will compromise from about 0.5 to 20% by weight of the formulation, favourably from about 1 to 10%, for example 2 to 5%.

The dose of the compound used in the treatment of the invention will vary in the usual way with the seriousness of the disorders, the weight of the sufferer, and the relative efficacy of the compound. However, as a general guide suitable unit doses may be 0.1 to 1000 mg, such as 0.5 to 200, 0.5 to 100 or 0.5 to 10 mg, for example 0.5, 1, 2, 3, 4 or 5 mg; and such unit doses may be administered more than once a day, for example 2, 3, 4, 5 or 6 times a day, but preferably 1 or 2 times per day, so that the total daily dosage for a 70 kg adult is in the range of about 0.1 to 1000 mg, that is in the range of about 0.001 to 20 mg/kg/day, such as 0.007 to 3, 0.007 to 1.4, 0.007 to 0.14 or 0.01 to 0.5 mg/kg/day, for example 0.01, 0.02, 0.04, 0.05, 0.06, 0.08, 0.1 or 0.2 mg/kg/day, and such therapy may extend for a number of weeks or months.

Assay Methods

The assays used to confirm the phosphodiesterase IV inhibitory activity of compounds of formula (I) are standard assay procedures as disclosed by Schilling et al, Anal. Biochem. 216:154 (1994), Thompson and Strada, Adv. Cycl. Nucl. Res. 8:119 (1979) and Gristwood and Owen, Br. J. Pharmacol. 87:91P (1986).

Compounds of formula (i) have exhibited activity at levels consistent with those believed to be useful in treating phosphodiesterase IV related disease states in those assays.

The ability of compounds of formula (i) to inhibit TNF production in human peripheral blood mononuclear cells (PMBC's) is measured as follows. PMBC's are prepared from freshly taken blood or "Buffy coats" by standard procedures. Cells are plated out in RPMI 1640+1% foetal calf serum in the presence and absence of inhibitors. LPS (Lipopolysaccharide (endotoxin); 100 ng/ml) is added and cultures are incubated for 22 h at 37° C. in an atmosphere of 95% air/5% $CO_2$. Supernatants are tested for TNFα by ELISA (Enzyme linked immunosorbent assay) using commercially available kits.

Activity in a guinea pig lung model is measured using the procedures described by Mauser et al, Am. Rev. Respir. Dis. 148:1623 (1993), and Am. J. Respir. Crit. Care Med. 152:467 (1995).

Example 6 of WO-A-98/22460 has an $IC_{50}$ 0.39 μM, whereas Example 5 herein (representative of the present invention) has $IC_{50}$ 0.017 μM.

The following Examples illustrate the invention.

INTERMEDIATE 1

2-Cyclopropyl-4-methoxybenzothiazole

2-Amino-4-methoxybenzothlazole (1.5 g) was heated at reflux for 20 hrs in 60% sodium hydroxide solution (100 ml). On cooling the reaction was poured into ice, acidified to pH 5 with 1M hydrochloric acid solution and extracted with toluene (3×150 ml). The combined organic extracts were washed with water (200 ml), dried over magnesium sulphate (15 g) and the solvent removed in vacuo to yield a green oil. This was combined with cyclopropane carboxylic acid (0.58 ml), 1,2-dichlorobenzene (30 ml) and trimethylsilylpolyphosphate (3 ml) and heated at reflux for 90 minutes. On cooling, water (15 ml) was added, the reaction basified to pH 8 using 2M sodium hydroxide solution, and extracted with dichloromethane (3×70 ml). The combined organic extracts were dried over magnesium sulphate (10 g) and the solvent removed in vacuo to yield a brown oil. This was purified by flash chromatography (eluent 50% ethyl acetate/heptane) to yield the title compound as a light brown oil (0.46 g). TLC $R_f$ 0.30 (30% ethyl acetate in hexane).

The following compound was prepared in a similar manner.

INTERMEDIATE 2

4-Methoxy-2-trifluoromethylbenzothiazole

Starting from 2-amino-4-methoxybenzothiazole (1.5 g) and trifluoroacetic acid (5.5 ml), without 1,2 dichlorobenzene. Purification by flash chromatography (eluent 20% ethyl acetate/hexane) yielded the title compound as a light brown oil (0.74 g). TLC $R_f$ 0.70 (50% ethyl acetate in hexane)

INTERMEDIATE 3

2-Ethyl-4-methozybenzothiazole

2-Amino-4-methoxybenzothiazole (4 g) was heated at reflux for 20 hrs in 60% sodium hydroxide solution (250 ml). On cooling the reaction was poured into ice, acidified to pH 5 with 1M hydrochloric acid solution and extracted with toluene (3×200 ml). The combined organic extracts were washed with water (300ml), dried over magnesium sulphate (20 g) and the solvent removed in vacuo to yield a green oil. This was combined with triethylorthopropionate (19.5 ml) and heated at 140° C. for 20 hrs. On cooling, water (100 ml) was added and the reaction extracted with ethyl acetate (2×50 ml). The combined organic extracts were dried over magnesium sulphate (10 g) and the solvent removed in vacuo to yield a brown oil. This was purified by flash chromatography (eluent 10–20% ethyl acetate/hexane to yield the title compound as a light brown oil (0.46 g). TLC $R_f$ 0.18 (20% ethyl acetate in hexane).

INTERMEDIATE 4

2-Bromo-4-methoxybenzothiazole

To a solution of 2-amino-4-methoxybenzothiazole (1.5 g) and potassium bromide (3.5 g) in sulphuric acid (1.25M, 50 ml) at 0° C. was added sodium nitrite (0.86 g) over a period of 1 hr. The reaction was allowed to warm to room temperature and stirred for 2 hrs, before being extracted with dichloromethane (3×50 ml). The combined organic extracts were dried over magnesium sulphate (5 g), and the solvent removed in vacuo to yield an off white solid. This was purified by flash chromatography (eluent 50% ethyl acetate/hexane) to yield the title compound as a white solid (1.6 g). TLC $F_f$ 0.30 (20% ethyl acetate in hexane)

INTERMEDIATE 5

7-Bromo-2-ethylimethoxybenzothiazole

To a stirred solution of 2-ethyl-4-methoxybenzothiazole (2.5 g) in acetonitrile (50 ml) was added N-bromosuccinamide (2.3 g). The reaction was stirred at room temperature for 20 hrs, before the acetonitrile was removed in vacuo, and the resulting residue purified by flash chromatography (eluent ethyl acetate) to yield the title compound as an off-white solid (2.9 g). TLC $R_f$ 0.60 (50% ethyl acetate in hexane).

The following compounds were prepared in a similar manner.

INTERMEDIATE 6

7-Bromo-2-cyclopropyl-4-metboxybenzothiazole

Starting from 2-cyclopropyl-4-methoxybenzothiazole (3 g), N-bromosuccinamide (0.17 g) and acetonitrile (30 ml). Purification by flash chromatography (eluent 30% ethyl acetate/heptane) yielded the title compound as an off-white solid (0.24 g). TLC $R_f$ 0.30 (30% ethyl acetate in heptane).

INTERMEDIATE 7

2,7-Dibromo-4-methoxybenzothiazole

Starting from 2-bromo-4-methoxybenzothiazole (1.6 g), N-bromosuccinamide (0.91 g) and acetonitrile (100 ml). Purification by flash chromatography (eluent 20% ethylacetate/hexane) yielded the title compound as an off-white solid (1.8 g). TLC $R_f$ 0.31 (20% ethyl acetate in heptane).

INTERMEDIATE 8

7-Bromo-4-methoxy-2-(morpholin-4-yl)benzothiazole

A suspension of 2,7-dibromo-4-methoxybenzothiazole (1.8 g) and morpholine (10 ml) in tetrahydrofuran (10 ml) was heated at 80° C. for 2 hours. The solvent was removed in vacuo and the residue partitioned between ethyl acetate (100 ml) and water (100 ml). The organic layer was dried over magnesium sulphate (3 g), filtered and the filtrate evaporated in vacuo to yield an off white solid. This was purified by recrystallisation from ethyl acetatelhexane to yield the title compound as a white solid (1.2 g). TLC $R_f$ 0.39 (50% ethyl acetate in hexane).

The following compounds were prepared in a similar manner.

INTERMEDIATE 9

7-Bromo-4-methoxy-2-(piperidin-1-yl)benzothiazole

Starting from 2,7-dibromomethoxybenzothiazole (15 g), piperidine (0.8 g) and tetrahydrofuran (20 ml). Purification by flash chromatography (eluent 50% ethylacetate/hexane) yielded the title compound as an off-white solid (1.5 g). TLC $R_f$ 0.67 (ethyl acetate).

INTERMEDIATE 10

7-Bromo-2-(4-tert-butoxycarbonylpiperazin-1-yl)-4-methoxybenzothiazole

Starting from 2,7-dibromo-4-methoxybenzothiazole (1.25 g), t-butyl-1-piperazine (1.6 g) and tetrahydrofuran (40 ml). Purification by flash chromatography (eluent 40–60% ethyl acetate/hexane) yielded the title compound as a pale yellow solid (1.5 g).TLC $R_f$ 0.49 (50 % ethyl acetate in hexane).

INTERMEDIATE 11

2-Ethyl-4-methoxybenzothiazole-7-carboxylic acid

A mixture of 7-bromo-2-ethyl-4-methoxybenzothiazole (2.96 g), palladium (II) acetate (240 mg), bis-diphenylphosphinopropane (900 mg), and triethylamine (15 ml) in tetrahydrofuran (150 ml) and water (20 ml) was charged with 150 psi of carbon monoxide and stirred at 90° C. for 3 days. The organic solvent was removed in vacuo and the residue partitioned between ethyl acetate (50 ml) and aqueous sodium hydroxide (1M, 2×50 ml). The aqueous extracts were combined, acidified to pH 4 with glacial acetic acid, extracted with ethyl acetate (3×50 ml). The organic extracts were combined, dried over magnesium sulphate (5 g), filtered, and the filtrate evaporated in vacuo Recrystallisation from ethyl acetate/hexane gave the desired product as an off-white solid (2.2 g). TLC $R_f$ 0.30 (50%ethyl acetate in hexane)

The following compounds were prepared in a similar manner.

INTERMEDIATE 12

2-Cyclopropyl-4-methoxybenzothiazole-7-carboxylic acid

Starting from 7-bromo-2-cyclopropyl-4-methoxybenzothiazole (515 mg), palladium (II) acetate (40 mg), bis-diphenylphosphinopropane (149 mg), and triethylamine (2.5 ml) in tetrahydrofuran (15 ml) and water (7 ml). Trituration of the residue with diethyl ether yielded the title compound as an off-white solid (360 mg). TLC $R_f$ 0.49 (ethyl acetate).

INTERMEDIATE 13

2-(Morpholin-4-yl)-4-methoxybenzothiazole-7-carboxylic acid

Starting from 7-bromo-2-(morpholin-4-yl)-4-methoxybenzothiazole (600 mg), palladium (II) acetate (41 mg), bis-diphenylphosphinopropane (150 mg), and triethylamine (2.5 ml) in tetrahydrofaran (100 ml) and water (10 ml). Recrystallisation fron ethyl acetate/hexane yielded the title compound as an off-white solid (395 mg). TLC $R_f$ 0.12 (50% ethyl acetate in hexane).

INTERMEDIATE 14

2-(Piperidin-1-yl)-4-methoxybenzothiazole-7-carboxylic acid

Starting from 7-bromo-2-(piperidin-1-yl)-4-methoxybenzothiazole (1.4 g), palladium (II) acetate (100 mg), bis-diphenylphosphinopropane (350 mg), and triethylamine (6 ml) in tetrahydrofuran (200 ml) and water (20 ml). Trituration of the residue with diethyl ether yielded the title compound as a yellow solid (700 mg). TLC $R_f$ 0.66 (ethyl acetate).

INTERMEDIATE 15

2-(4-tert-Butoxycarbonylpiperazin-1-yl)-4-methoxybenzo-thiazole-7-carboxylic acid Starting from 7-bromo-2-(4-tert-butoxycarbonylpiperazin-1-yl)-4-methoxybenzothiazole (1.5 g), palladium (II) acetate (85 mg), bis-diphenylphosphinopropane (310 mg), and triethylamine (5.3 ml) in tetrahydrofuran (60 ml) and water (30 ml). Purification by column chromatography (eluent 20% ethyl acetate in heptane) yielded the title compound as an off-white solid (290 mg). TLC $R_f$ 0.16 (50% ethyl acetate in hexane).

INTERMEDIATE 16

4-Metboxy-2-trifluoromethylbenzothiazole-7-carboxylic acid

4-Methoxy-2-trifluoromethylbenzothiazole (1.5 g) was dissolved in dichloromethane (30 ml) and cooled to 0° C. and treated with titanium tetrachloride (1.0M solution in dichloromethane, 13.8 ml). Dichloromethyl methyl ether (0.62 ml) was then added dropwise and the reaction stirred at 0° C. for 30 minutes, room temperature for 1 hr and reflux for 1 hr. On cooling the reaction was poured into ice and the reaction extracted with dichloromethane (2×100 ml). The combined organic extracts were dried over magnesium sulphate (5 g) and the solvent removed in vacuo to yield a brown oil. This was dissolved in tert-butanol (40 ml) and 2-methyl-2-butene (3.5 ml) was added. Sodium phosphate (4.7 g) and sodium chlorite (3.2 g) were then added and the reaction stirred at room temperature for 16 hrs. Water (10 ml) was added and the solvent was removed in vacuo, and the residue basified to pH8 with potassium hydroxide. The aqueous was extracted with dichworomethane (3×30 ml), before being acidified with 1M hydrochloric acid to pH6, and extracted with ethyl acetate (3×30 ml). The combined ethyl acetate extracts were dried over magnesium sulphate (5 g) and the solvent removed in vacuo to yield the title compound as a white solid (0.14 g). TLC $R_f$ 0.55 (50% ethyl acetate in hexane).

INTERMEDIATE 17

Methoxy-2-trifluoromethylbenzothiazole-7-carboxylic acid 4-nitrophenyl ester

A suspension of 4-methoxy-2-trifluoromethylbenzothiazole-7-carboxylic acid (140 mg) in dichloromethane (10ml) was treated with p-nitrophenol (72 mg), dimethylaminopyridine (catalytic) and 1-(3-dimethylaminopropyl)-3-ethyl carbodimide hydrochloride (150 mg). The mixture was stirred at room temperature for 12 hours and the reaction washed with water (10 ml). The organic layer was separated, dried over magnesium sulphate (5 g) and evaporated in vacuo. Purification by flash chromatography (eluent 50% ethyl acetate/hexane) yielded the title compound as an off-white solid (150 mg). TLC $R_f$ 0.13 (50% ethyl acetate in heptane).

The following compounds were prepared in a similar manner.

INTERMEDIATE 18

2-Cyclopropyl-4-methoxybenzothiazole-7-carboxylic acid 4-nitrophenyl ester

Starting from 2-cyclopropyl-4-methoxybenzothiazole-7-carboxylic acid (270 mg), p-nitrophenol (165 mg), and 1-(3-dimethylaminopropyl)-3-ethyl carbodiimide hydrochloride (228 mg) in dichloromethane (35 ml). Trituration of the residue with diethyl ether yielded the title compound as a bright yellow solid (290 mg). TLC $R_f$ 0.60 (ethyl acetate).

INTERMEDIATE 19

2-(Piperidin-1-yl)-4-methoxybenzothiazole-7-carboxylic acid 4-nitrophenyl ester

Starting from 2-(piperidin-1-yl)-4-methoxybenzothiazole-7-carboxylic acid (190 mg), p-nitrophenol (100 mg), and 1-(3-dimethylaminopropyl)-3-ethyl carbodiimide hydrochloride (150 mg) in dichloromethane (20 ml). Purification by column chromatography (eluent 50% ethylacetate in hexane) yielded the title compound as an off-white solid (240 mg). TLC $R_f$ 0.39 (50% ethyl acetate in hexane).

INTERMEDIATE 20

2-(4-tert-Butolycarbonylpiperazin-1-yl)-4-methoxybenzothiazole-7-carboxylic acid 4-nitrophenyl ester Starting from 2-(4-tert-butoxycarbonylpiperazin-1-yl)-4-methoxybenzothiazole-7-carboxylic acid (500 mg), p-nitrophenol (190 mg), and 1-(3-dimethylaminopropyl)-3-ethyl carbodiimide hydrochloride (370 mg) in dichioromethane (30 ml). Purification by column chromatography (eluent ethyl acetate) yielded the title compound as an off-white solid (460 mg). TLC $R_f$ 0.28 (50% ethyl acetate in hexane).

EXAMPLE 1

2-Ethyl-4-methoxybenzothiazole-7-carboxylic acid (3,5-dimethylisoxazol-4-yl)amide To a suspension of 2-ethyl-4-methoxybenzothiazole-7-carboxylic acid (0.1 g) in dichloromethane (10 ml) was added oxalyl chloride (0.08 ml) and dimethylformanide (1 drop). The reaction was stirred at room temperature for 16 hrs, and then the solvent was removed in vacuo to yield a brown solid residue. This was taken up in dichloromethane is (30 ml) and 3,5-dimethylisoxazol-4-amine (0.05 g) was added followed by triethylamine (0.15 ml) and the reaction stirred at room temperature for 16 hrs. The solvent was removed in vacuo and the product purified by flash chromatography (eluent ethyl acetate) to yield the title compound as an off-white solid (0.016 g). TLC $R_f$ 0.38 (ethyl acetate); Mpt 85–87° C.

The following compounds were prepared in a similar manner.

EXAMPLE 2

4Methoxy-2-(morpholin-4-yl)benzothiazole-7-carboxylic acid (3,5-dimethylisoxaol-4-yl)amide Starting from 4-methoxy-2-(morpholin-4-yl) benzothiazole-7-carboxylic acid (0.13 g), oxalyl chloride (2.0 ml), dichloromethane (10 ml) and dimethylformamide (1 drop), followed by 3,5-dimethylisoxazol-4-amine (0.05 g), triethylamine (0.1 ml) and dichloromethane (10 ml). Purification by flash chromatography (eluent 50% ethyl acetate/hexane-ethyl acetate) yielded the title compound as an off-white solid (0.066 g). TLC $R_f$ 0.40 (ethyl acetate); Mpt 326–327° C.

EXAMPLE 3

2-Cyclopropyl-4-methoxybenzothiazole-7-carboxylic acid (3,5-dimethylisoxazol-4-yl)amide Starting from 2-cyclopropyl-4-methoxybenzothiazole-7-carboxylic acid (0.20 g), oxalyl chloride (0.11 ml), dichloromethane (30 ml) and dimethylformamide (1 drop), followed by 3,5-dimethylisoxazol-4-amine (0.20 g), triethylamine (0.22 ml) and dichloromethane (30 ml). Purification by flash chromatography (eluent 50% ethyl acetate/heptane) yielded the title compound as a white solid (0.067 g). TLC $R_f$ 0.33 (ethyl acetate); Mpt 196–197° C.

EXAMPLE 4

4-Methoxy-2-(piperidin-1-yl)benzothiazole-7-carboxylic acid (3,5-dimethyiisoxazol-4-yl)amide Starting from 4-methoxy-2(piperidin-1-yl)benzothiazole-7-carboxylic acid (0.24 g), oxalyl chloride (2.0 ml), dichloromethane (20 ml) and dimethylformamide (1 drop), followed by 3,5-dimethylisoxazol-4-amine (0.10 g), triethylamine (0.25 ml) and dichloromethane (20 ml). Purification by flash chromatography (eluent 5% methanol in dichloromethane) yielded the title compound as a white solid (29 mg). TLC $R_f$ 0.49 (ethyl acetate); MS found M+1 387.

EXAMPLE 5

2-Ethyl-4-methoxybenzothiazole-7-carboxylic acid (2-methyl-2H-pyrazol-3-yl)amide Starting from 2-ethyl-4-methoxybenzothiazole-7-carboxylic acid (0.2 g), oxalyl chloride (0.15 ml), dichloromethane (20 ml) and dimethylformamide (1 drop), followed by 2-methyl-2H-pyrazol-3-ylamine (0.17 g), triethylamine (0.24 ml) and dichloromethane (40 ml). Purification by flash chromatography (eluent 10% methanol/dichloromethane) yielded the title compound as a yellow solid (0.08 g). TLC $R_f$ 0.52 (10% methanol in dichloromethane), Mpt 185–186° C.

EXAMPLE 6

2-(4-tert-Butoxycarbonylpiperazin-1-yl)-4-methoxybenzothiazole-7-carboxylic acid (3,5-dimethylisoiazol-4-yl)amide Starting from 2-(4-tert-butoxycarbonylpiperazin-1-yl)-4-methoxybenzothiazole-7-carboxylic acid (0.11 g), oxalyl chloride (0.06 ml), dichloromethane (10 ml) and dimethylformamide (1 drop), followed by 3,5-dimethylisoxazol-4-amine (70 mg), triethylamine (0. 08 ml) and dichloromethane (10 ml). Purification by flash chromatography (eluent 75% ethyl acetate in hexane) yielded the title compound as a yellow solid (29 mg). TLC $R_f$ 0.51 (ethyl acetate); Mpt 231–233° C.

EXAMPLE 7

2-Ethyl-4-methoxybenzothiazole-7-carboxylic acid (4-cyano-2-methyl-2H-pyrazol-3-yl)amide To a suspension of 2-ethyl-4-methoxybenzothiazole-7-carboxylic acid (0.1 g) in dichloromethane (10 ml) was added oxalyl chloride (1.0 ml) and dimethylformamide (1 drop). The reaction was stirred at room temperature for 16 hrs, and then the solvent was removed in vacuo to yield a brown solid residue. 5-Amino-1-methyl-1H-pyrazole-4-carbonitrile (0.1 g) was taken up in dichloromethane (10 ml) and sodium hexamethyldisilylamine (1.0M in tetrahydrofuran, 0.84 ml) was added. After 5 minutes the acid chloride was added and the reaction stirred at room temperature for 16 hrs. The solvent was removed in vacuo and the product purified by flash chromatography (eluent 50% ethyl acetatethexane-75% ethyl acetate/hexane) to yield the title compound as an off-white solid (0.088 g). TLC $R_f$ 0.13 (50% ethyl acetate/hexane); Mpt 190–191° C.

The following compound was prepared in a similar manner.

EXAMPLE 8

4Methoxy-2-(morpholin-4-yl)-benzothiazole-7-carboxylic acid (4-cyano-2-methyl-2H-pyrazol-3-yl)amide Starting with 4-methoxy-2-(morpholin-4-yl)benzothiazole-7-carboxylic acid (0.13 g) oxalyl chloride (0.10 ml), dichloromethane (10 ml) and dimethylformamide (1 drop), followed by 5-amino-1-methyl-1H-pyrazole-4-carbonitrile (0.11 g), sodium hexamethyldisilylamine (1.0M in tetrahydrofuran, 0.88 ml) and dichloromethane (10 ml). Purification by flash chromatography (eluent ethyl acetate) yielded the title compound as an off-white solid (0.02 g). TLC $R_f$ 0.45 (ethyl acetate); Mpt 299–300° C.

EXAMPLE 9

4-Methoxy-2-trifluoromethylbenzothiazole-7-carboxylic acid (4-cyano-2-methyl-2H-pyrazol-3-yl)amide A solution of 5-amino-1-methyl-1H-pyrazole-4-carbonitrile (93 mg) in dimethyl formamide (10 ml) was treated with a solution of sodium hexamethyldisilazide in tetrahydrofuran (0.76 ml, 1.0M). After three minutes the mixture was treated with 4-methoxy-2-trifluoromethylbenzothiazole-7-carboxylic acid 4-nitrophenyl ester (150 mg) and the reaction stirred at room temperature for 2 hours. The solvent was removed in vacuo. Purification by flash chromatography (eluent ethyl acetate) to yield the title compound as an off-white solid (50 mg). TLC $R_f$ 0.48 (ethyl acetate); MS found M+1 382.

The following compounds were prepared in a similar manner.

EXAMPLE 10

2-Cyclopropyl-4-methoxybenzothiazole-7-carboxylic acid (4-cyano-2-methyl-2H-pyrazol-3-yl)amide Starting from 5-amino-1-methyl-1H-pyrazole-4-carbonitrile (90 mg) in dimethyl formamide (30 ml), sodium hexamethyldisilazide in tetrahydrofbran (1.08 ml, 1.0 M), and 2-cyclopropyl-4-methoxybenzothiazole-7-carboxylic acid 4-nitrophenyl ester (200 mg). Purification by flash chromatography (eluent 10% methanol in dichloromethane) to yield the title compound as an off-white solid (95 mg). TLC $R_f$ 0.30 (10% methanol in dichloromethane); Mpt 259–260° C.

EXAMPLE 11

4Methoxy-2-(piperidin-1-yl)benzothiazole-7-carboylic acid (4-cyano-2-methyl-2H-pyrazol-3-yl)amide Starting from 5-amino-1-methyl-1H-pyrazole-4-carbonitrile (125 mg) in dimethyl formamide (10 ml), sodium hexamethyldisilazide in tetrahydrofuran (1.1 ml, 1.0 M), and 4-methoxy-2-(piperidin-1-yl)benzothiazole-7-carboxylic acid 4-nitrophenyl ester (210 mg). Purification by flash chromatography (eluent 5% methanol in dichloromethane) followed by trituration with ethyl acetate yielded the title compound as an off-white solid (152 mg). TLC $R_f$ 0.48 (ethyl acetate); Mpt 290–291° C.

EXAMPLE 12

2-(4-tert-Butoxycarbonylpiperazin-1-yl)-4-methoxybenzothiazole-7-carboxylic acid (4-cyano-2-methyl-2H-pyrazol-3-yl)amide Starting from 5-amino-1-methyl-1H-pyrazole-4-carbonitrile (119 mg) in dimethyl fonnamide (10 ml), sodium hexamethyldisilazide in tetrahydrofuran (0.97 ml, 1.0 M), 2-(4-tert-butoxycarbonylpiperazin-1-yl)-4-methoxybenzothiazole-7-carboxylic acid 4-nitrophenyl ester (250 mg). Purification by flash chromatography (eluent 5% methanol in dichloromethane) followed by trituration with diethyl ether yielded the title compound as a pale yellow solid (260 mg). TLC $R_f$ 0.48 (ethyl acetate); Mpt 231–232° C.

EXAMPLE 13

4-Methoxy-2-(piperazin-1-yl)benzothiazole-7-carboxylic acid (4-cyano-2-methyl-2H-pyrazol-3-yl) amide, trifluoroacetic acid salt A solution of 2-(4-tert-butoxycarbonylpiperazin-1-yl) methoxybenzothiazole-7-carboxylic acid (4-cyano-2-methyl-2H-pyrazol-3-yl)amide (260 mg) and dicloromethane (10 ml) was treated with trifluoroacetic acid and the mixture stirred at room temperature for one hour. The solvent was removed in vacuo and the residue triturated with diethyl ether to yield the title compound as a yellow solid (285 mg). TLC $R_f$ 0.09 (10% methanol in dichnoromethane); Mpt 242–244° C.

The following compounds were prepared in a similar manner.

EXAMPLE 14

4-Methoxy-2-(piperazin-1-yl)benzothiazole-7-carboxylic acid (3,5dimethylisoxazol-4-yl)amide, trifluoroacetic acid salt Starting from 2-(4-tert-butoxycarbonylpiperazine-1-yl)-4-methoxybenzothiazole-7-carboxylic acid (3,5-dimethylisoxazol-4-yl)amide (0.24 g), trifluoroacetic acid (2.0 ml), and dichloromethane (20 ml). Trituration with diethyl ether yielded the title compound as a white solid (2 mg). TLC $R_f$ 0.01 (10% methanol in dichloromethane).

EXAMPLE 15

4-Methoxy-2-(4-methylpiperazin-1-yl) benzothiazole-7-carboxylic acid (4-cyano-2-methyl-2H-pyrazol-3-yl)amide A suspension of 4-methoxy-2-(piperazin-1-yl) benzothiazole-7-carboxylic acid (4-cyano-2-methyl-2H-pyrazol-3-yl)amide trifluoroacetic acid salt (275 mg) in acetonitrile (20 ml) was treated with formaldehyde (0.44 ml, 37% aqueous solution), sodium cyanoborohydride (102 mg), and acetic acid (0.3 ml) and the mixture stirred at room temperature of 12 hours. The solvent was evaporated in vacuao and the residue partitioned between aqueous sodium hydroxide (10 ml, 1M) and dichloromethane (100 ml). The aqueous layer was separated, was neutralised with acetic acid, and extracted with 2% methanol in dichloromethane (2×75 ml). The extracts were combined, dried over magnesium sulphate (5 g), filtered, and the filtrate evaporated in vacuo. Purification by column chromatography (eluent 5% methanol in dichloromethane) followed by trituration with diethyl ether yielded the title compound as a pale yellow solid (40 mg). TLC $R_f$ 0.14 (10% methanol in dichloromethane); Mpt 249–251° C.

What is claimed is:

1. A compound of the formula (i)

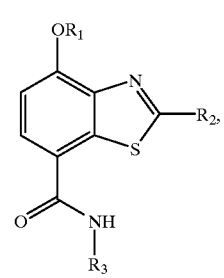

wherein $R_1$ is $C_{3-6}$ cycloalkyl, or $C_{1-3}$ alkyl optionally substituted with one or more fluorine atoms;

$R_2$ is $C_{1-6}$ alkyl, $C_{3-6}$ cycloalkyl, $CF_3$, $CH_2CF_3$, $C_2F_5$ or $NR_4R_5$;

$R_3$ is a pyrazole, imidazole or isoxazole group of partial formula (A), (B) or (C)

(A)

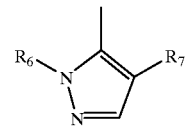

(B)

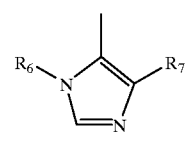

(C)

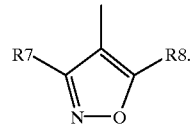

$NR_4R_5$ is a nitrogen-containing heterocyclic ring;

$R_6$ is $C_{1-3}$ alkyl; and $R_7$ and $R_8$, which are the same or different, are each H, $C_{1-3}$ alkyl, halogen, $CF_3$ or CN, provided that both are not H;

or a pharmaceutically-acceptable salt thereof.

2. The compound of claim 1, wherein $R_3$ is a pyrazole or isoxazole group.

3. The compound of claim 2, wherein $R_3$ is a pyrazole group, $R_6$ is $CH_3$ and $R_7$ is CN, $CH_3$ or $CF_3$.

4. The compound of claim 2, wherein $R_3$ is an isoxazole group and $R_7$ and $R_8$ are independently selected from $CH_3$, $CF_3$ and CN.

5. The compound of claim 1, wherein $R_1$ is optionally F-substituted alkyl and $R_2$ is alkyl, cycloalkyl, $CF_3$ or $NR_4R_5$.

6. The compound of claim 5, wherein $R_1$ is $CH_3$ or $CHF_2$.

7. The compound of claim 5, wherein $R_2$ is $CF_3$, ethyl or cyclopropyl.

8. The compound of claim 6, wherein $R_2$ is $CF_3$, ethyl or cyclopropyl.

9. The compound of claim 1, selected from the group consisting of 2-ethyl-4-methoxybenzothiazole-7-carboxylic acid (3,5-dimethylisoxazol-4-yl) amide, 4-methoxy-2-(morpholin-4-yl)-benzothiazole-7-carboxylic acid (3,5-dimethylisoxazol-4-yl)amide, 2-cyclopropyl-4-methoxybenzothiazole-7-caboxylic acid (3,5-dimethylisoxazol-4-yl)amide, 4-methoxy-2-(piperidin-1-yl)-benzothiazole-7-carboxylic acid (3,5-dimethylisoxazol-4-yl)amide, 2-ethyl-4-methoxybenzothiazole-7-carboxylic acid (2-methyl-2H-pyrazol-3-yl)amide, 2-(4-tert-butoxycarbonylpiperazin-1-yl)-4-methoxybenzothiazole-7-caboxylic acid (3,5-dimethylisoxazol-4-yl)amide, 2-ethyl-4-methoxybenzothiazole-7-caboxylic acid (4-cyano-2-methyl-2H-pyrazol-3-yl)amide 4-methoxy-2-(morpholin-4-yl)-benzothiazole-7-carboxylic acid (4-cyano-2-methyl-2H-pyrazol-3-yl)-amide, 4-methoxy-2-(piperidin-1-yl)benzothiazole-7-carboxylic acid (4-cyano-2-methyl-2H-pyrazol-3-yl)amide, 2-(4-tert-butoxycarbonylpiperazin-1-yl)-4-methoxyenzothiazole-7-oxylic acid (4-cyano-2-methyl-2H-pyrazol-3-yl)amide, 4-methoxy-2-(piperazin-1-yl)benzothiazole-7-carboxylic acid (4-cyano-2-methyl-2H-pyrazol-3-yl)amide, trifluoroacetic acid salt, 4-methoxy-2-(piperazin-1-yl)benzothiazole-7-carboxylic acid (3,5-dimethylisoxazol-4-yl)amide, trifluoroacetic acid salt, and 4-methoxy-2-(4-methylpiperazin-1-yl)benzothiazole-7-carboxylic acid (4-cyano-2-methyl-2H-pyrazol-3-yl) amide.

10. The compound of claim 1, selected from the group consisting of 4-methoxy-2-trifluoromethylbenzothiazole-7-carboxylic acid (4-cyano-2-methyl-2H-pyrazol-3-yl)amide and 2-cyclopropyl-4-methoxybenzothiazole-7-carboxylic acid (4-cyano-2-methyl-2H-pyrazol-3-yl)amide.

11. A composition for use in therapy, comprising a compound of claim 1 and a pharmaceutically acceptable carrier or diluent.

12. A method for the treatment of a disease state that is capable of being modulated by inhibition of phosphodiesterase IV or Tumour Necrosis Factor, or that is a pathological condition associated with a function of phosphodiesterase IV, eosinophil accumulation or a function of the eosinophil, said method comprising administering to a person or animal an effective amount of the compound of claim 1.

13. The method of claim 12, wherein the disease state is an inflammatory disease or autoimmune disease.

14. The method of claim 12, wherein the disease state is selected from the group consisting of asthma, chronic bronchitis, chronic pulmonary inflammatory disease, chronic obstructive airways disease, atopic dermatitis, allergic rhinitis, psoriasis, arthritis, rheumatoid arthritis, joint inflammation, ulcerative colitis, Crohn's disease, atopic eczema, stroke, bone resorption disease, multiple sclerosis and inflanmmatory bowel disease.

15. The method of claim 12, wherein the disease state is selected from the group consisting of urticaria, allergic conjunctivitis, vernal conjunctivitis, inflammation of the eye, allergic responses in the eye, eosinophilic granuloma, gouty arthritis and other arthritic conditions, adult respiratory distress syndrome, diabetes insipidus, keratosis, cerebral senility, multi-infarct dementia, senile dementia, memory impairment associated with Parkinson's disease, depression, cardiac arrest, intermittent claudication, rheumatoid spondylitis, osteoarthritis, sepsis, septic shock, endotoxic shock, gram negative sepsis, toxic shock syndrome, acute respiratory distress syndrome, cerebral malaria, silicosis, pulmonary sarcoidosis, reperfusion injury, graft vs host reaction, allograft rejection, infection-related fever or myalgia, malaria, HIV, AIDS, ARC, cachexia, keloid formation, scar tissue formation, pyresis, systemic lupus erythematosus, type 1 diabetes mellitus, Bechet's disease, anaphylactoid purpura nephritis, chronic glomerulonephritis, leukaemla, tarditive dyskinesia, yeast or fungal infection, conditions requiring gastroprotection, and neurogenic inflammatory disease associated with irritation and pain.

16. The method of claim 12, wherein the disease state is asthma.

17. The method of claim 12, wherein the disease state is chronic obstructive airways disease or chronic bronchitis.

\* \* \* \* \*

UNITED STATES PATENT AND TRADEMARK OFFICE
CERTIFICATE OF CORRECTION

PATENT NO.     : 6,313,116 B1
DATED          : November 6, 2001
INVENTOR(S)    : Hazel Joan Dyke, Andrew Sharpe, Hannah Jayne Kendall, Richard John Davenport, Verity Margaret Sabin, George Martin Buckley, Marianna Dilani Richard and Alan Findlay Haughan It is certified that error appears in the above-identified patent and that said Letters Patent is hereby corrected as shown below:

<u>Column 17,</u>
Line 20, "2-(4-*tert*-butoxycarbonylpiperazin-1-yl)-4-methoxybenzothiazole-7-caboxylic acid (3,5-dimethylisoxazol-4-yl)amide," should read -- 2-(4-*tert*-butoxycarbonylpiperazin-1-yl)-4-methoxybenzothiazole-7-carboxylic acid (3,5-dimethylisoxazol-4-yl)amide, --.

Line 22, "2-ethyl-4-methoxybenzothiazloe-7-caboxlic acid (4-cyano-2-methyl-2H-pyrazol-3-yl)amide," should read -- 2-ethyl-4-methoxybenzothiazole-7-carboxylic acid (4-cyano-2-methyl-2H-pyazol-3-yl)amide, --.

Lines 30-31, "2-(4-*tert*-butoxycarbonylpiperazin-l-yl)-4-methoxyenzothiazole-7-oxylic acid (4-cyano-2-methyl-2H-pyrazol-3-yl)amide," should read -- 2-(4-*tert*-butoxycarbonylpiperazin-1-yl)-4-methoxybenzothiazole-7-carboxylic acid (4-cyano-2-methyl-2H-pyrazol-3-yl)amide, --.

<u>Column 18,</u>
Line 20, "inflanmmatory "should read -- inflammatory --.
Line 39, "leukaemla" should read -- leukaemia --.

Signed and Sealed this

Twenty-seventh Day of August, 2002

*Attest:*

*Attesting Officer*

JAMES E. ROGAN
*Director of the United States Patent and Trademark Office*